United States Patent [19]

Johnson et al.

[11] 4,211,765

[45] Jul. 8, 1980

[54] METHOD FOR CONTROLLING OBESITY

[75] Inventors: John H. Johnson, Kirkwood; Joseph E. Fields, Ballwin, both of Mo.

[73] Assignee: Monsanto Company, St. Louis, Mo.

[21] Appl. No.: 945,720

[22] Filed: Sep. 25, 1978

Related U.S. Application Data

[60] Continuation-in-part of Ser. No. 572,799, Apr. 29, 1975, Pat. No. 4,117,111, which is a division of Ser. No. 353,832, Apr. 23, 1973, Pat. No. 3,923,972, which is a continuation-in-part of Ser. No. 188,577, Oct. 12, 1971, abandoned, which is a continuation-in-part of Ser. No. 789,081, Jan. 2, 1969, abandoned.

[51] Int. Cl.² ............................................. A61K 31/74
[52] U.S. Cl. ...................................................... 424/78
[58] Field of Search .......................................... 424/78

[56] References Cited

U.S. PATENT DOCUMENTS 3,655,869  4/1972  Wharton et al. ...................... 424/78

*Primary Examiner*—Frederick E. Waddell
*Attorney, Agent, or Firm*—Joseph D. Kennedy; James W. Williams, Jr.

[57] ABSTRACT

The invention involves a method of weight control in which polymers of unsaturated carboxylic acid derivatives are orally administered to interfere with assimilation of fat. Polymers which inhibit action of pancreatic lipase, especially cationic polymers such as dialkylaminoalkyl imides of alkene/maleic anhydride copolymers, are particularly useful.

4 Claims, No Drawings

METHOD FOR CONTROLLING OBESITY

REFERENCE TO RELATED APPLICATIONS

This application is continuation-in-part of our application Ser. No. 572,799 filed Apr. 29, 1975, now U.S. Pat. No. 4,117,111, which is a division of our copending application Ser. No. 353,832, filed Apr. 23, 1973 now U.S. Pat. No. 3,923,972 which in turn is a continuation-in-part of our copending application Ser. No. 188,577, filed Oct. 12, 1971, now abandoned, which, in turn is a continuation-in-part of our copending application Ser. No. 789,081, now abandoned, filed Jan. 2, 1969. The said application Ser. No. 353,832 subsequently issued as U.S. Pat. No. 3,923,972 on Dec. 2, 1975 and re-issued as U.S. Re. Pat. No. 29,652 from Ser. No. 701,713 filed July 1, 1976.

BACKGROUND OF THE INVENTION

Human obesity or overweight is a recognized health problem. The accumulation or maintenance of body fat bears a direct relationship to caloric intake. Most weight control programs involve some restriction or alteration of the diet. However, there have also been various proposals to alter or interfere with the body's mechanism for utilizing food, as for example by an intestinal by-pass operation. Also the use of fat absorption inhibitors for the purpose of weight control has been proposed, as in the use of inhibitors of the enzyme intestinal alkaline phosphatase in U.S. Pat. No. 3,809,752. In application Ser. No. 353,832 (now U.S. Pat. No. 3,923,972) and other applications referenced above, polymeric materials are described as useful for controlling blood cholesterol levels, and evidence indicates that this effect is achieved by interference with absorption or transport of fats in the diet, particularly as it relates to assimilation of cholesterol.

SUMMARY OF THE INVENTION

It has been found that certain classes of polymeric materials can have a favorable influence on body weight by affecting assimilation of dietary fat. In a particular aspect it has been found that certain types of polymers are capable of inhibiting the action of pancreatic lipase, thereby retarding the breakdown and assimilation of dietary fat in the gastro-intestinal tract.

The polymeric fat absorption inhibitors when orally administered induce a degree of steatorrhea manifesting lower fat absorption and an increase in fecal fat. While the polymers herein are characterized in terms of chemistry, structure, composition, etc., one of the significant aspects of the polymers is the ability to increase fat excretion upon oral administration.

It is an object of the present invention to provide a method of weight control, particularly with respect to having a retarding or lowering influence on body weight. The invention is useful for retarding undesirable weight increases and maintaining a desirable weight level in subjects in need of such control, as well as in effecting reduction of weight in subjects where reduction is indicated. The use of the polymers makes it possible to keep the weight at lower levels than would obtain in the absence of such treatment.

Extensive work has been published discussing the mechanism by which fats and other lipids are absorbed from the intestines. The pancreatic lipase is believed to be effective in causing a partial hydrolysis of glycerides to obtain fatty acids and monoglycerides which together with the bile acids form complexes which are taken up by the intestinal mucosa. Thus if the lipolytic action of the pancreatic lipase is inhibited, the absorption of the fatty materials is also inhibited. In one aspect the present invention employs polymers which have manifest ability to inhibit pancreatic lipase under physiological conditions, and such materials generally have corresponding effectiveness in inhibiting fat absorption. However, there are apparently other mechanisms by which polymeric materials may inhibit fat absorption, and some materials are effective absorption inhibitors even though normal physiological conditions may neutralize their pancreatic lipase inhibiting ability.

The polymers utilized in the present invention are non-systemic, i.e., they apparently are effective in the gastrointestinal tract and are not appreciably absorbed through the intestinal wall into the blood stream. The essentially non-systemic nature is considered advantageous in that it lessens the possibilities for unnecessary interference with body processes and functions and potential side effects. Purification procedures can be used to remove low molecular weight polymer or residual monomer fractions which conceivably may have a greater tendency toward absorption.

The present invention involves orally administering to a living animal body a pharmaceutically effective amount of a polymer selected from the group consisting of (1) a polymerized unsaturated carboxylic acid, or anhydride (2) a copolymer of (a) an unsaturated monomer having, for example, 2 to 30 carbon atoms, and (b) an unsaturated carboxylic acid, anhydride or derivative thereof. By this method the fat excretion in living animal bodies, including warm-blooded vertebrate animals, such as chickens, dogs, cats, cattle, swine and primates, for example monkeys, is effectively increased.

The polymer can be orally administered to the living animal body by any suitable means, and in any suitable form. For example, the polymer can be incorporated into ordinary foodstuffs and beverages containing nutritional values in an amount sufficient to produce the desired effect. Also, the polymer can be incorporated into a pharmaceutical composition of the form customarily employed for oral administration. Pharmaceutical compositions containing the polymer may be in liquid form, for example, a solution or suspension specifically adapted for oral administration or in solid form, for example, a tablet, capsule, pill or packaged powder. Advantageously, the pharmaceutical composition containing the polymer can be prepared in unit dosage form using pharmaceutically acceptable carriers, such as, for example, starch, glucose, lactose, gelatin, sucrose, etc., and the like. If desired, the dosage unit can be made up in a sustained release form to give a controlled dosage over an extended period of time.

The amount of dosage of polymer administered to the living animal body will, of course, vary depending among other things, on the size of the living animal body, the particular living animal body to be treated, and the general health of the living animal body, and any pharmaceutically effective amount may be employed. The dosage can be determined with regard to established medical practice. Generally the amount of polymer administered on a daily basis is in the range of from about 0.01 to about 5.0% of the total diet, and often in the range of from about 0.05 to about 3.0%, but with some of the more effective polymers it may be appropriate to use less than 0.5% or even less than 0.1%, say 0.005% to 0.05%, or about 0.005 to about 0.1%.

The polymers employed in the method of the present invention, are (1) polymerized unsaturated carboxylic acids or anhydrides, (2) copolymers of (a) an unsaturated monomer having, for example, 2 to 30 carbon atoms, and (b) an unsaturated carboxylic acid anhydride or unsaturated carboxylic acid derivative, preferably having a weight average molecular weight of at least about 3,000.

The polymer may advantageously be an EMA-type polymer.

Among the EMA-type polymers suitable for the practice of the instant invention are polymers and pharmaceutically acceptable salts of polymers having units of the formula.

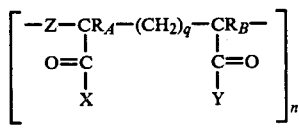

wherein:

$R_A$ and $R_B$ are selected from the group consisting of hydrogen, halogen (preferably chlorine), alkyl of 1 to 4 carbon atoms (preferably methyl), cyano, phenyl, or mixtures thereof; provided that not more than one of $R_A$ and $R_B$ is phenyl; Z is a bivalent radical (preferably alkylene, phenylalkylene, alkoxyalkylene, alkylcarboxyalkene and aliphatic acyloxyalkylene) of 1 to 30 carbon atoms, q is zero or one, X and Y are selected from hydroxy, —O alkali metal, OR, —OH—NH$_3$, —OH—R$_3$N, —OH—R$_2$NH, —OH—RNH$_2$, —NRR', —ONR$_4$, —(Q)$_p$—W—(NR'R')$_x$ and —(Q)$_p$—W—(—OH)$_x$, wherein x is 1 to 4 and p is zero or one, wherein R is selected from the group consisting of hydrogen, alkyl, phenylalkyl, or phenyl, in each case of 1 to 18 carbon atoms, wherein R' is H or R, wherein Q is oxygen or —NR'—, and wherein W is a bivalent radical preferably selected from alkylene, phenylene, alkylene amine and phenylalkylene having up to 20 carbon atoms, X and Y taken together can be oxygen or

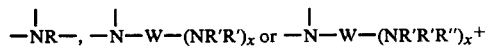

wherein R, W, R' have the meanings previously assigned and R" is alkyl of 1 to 18 carbon atoms, benzyl or aromatic-substituted benzyl. The units of the formula given above are recurring n being at least 8 and can be as much as 100,000 degrees of polymerization. When the units are recurring the symbols in the various recurring units do not necessarily stand for the same thing in all of the recurring units.

Many of these polymers suitable for the practice of the present invention or suitable after conversion to derivatives are commercially available.

The polycarboxylic acid polymers can be of the non-vicinal-type including those containing monomer units, such as acrylic acid, acrylic anhydride, methacrylic acid, crotonic acid or their respective derivatives, including partial salts, amides and esters or of the vicinal type, including maleic, itaconic, citraconic, a-dimethyl maleic, a-butyl maleic, a-phenyl maleic, fumaric, aconitic, a-chloromaleic, a-bromomaleic, a-cyanomaleic acids including their salts, amides and esters. Anhydrides of the foregoing acids are also advantageously employed.

Co-monomers suitable for use with the above polycarboxylic acid monomers include α-olefins, such as ethylene, 2-methyl-pentene-1, propylene, butylene, 1- or 2-butene, 1-hexene, 1-octene, 1-decene, 1-dodecene, 1-octadecene, and other vinyl monomers, such as styrene, a-methyl styrene, vinyltoluene, vinyl acetate, vinyl chloride, vinyl formate, vinyl alkyl ethers, e.g., methylvinylether, alkyl acrylates, alkyl methacrylates, acrylamides, methacrylamides, alkylmethacrylamides and alkylacrylamides, or mixtures of these monomers. Reactivity of some functional groups in the copolymers resulting from some of these monomers permits formation of other useful functional groups in the formed copolymer, including hydroxy, lactone, amine and lactam groups.

Any of the said carboxylic acids or derivatives, may be copolymerized with any of the other monomers described above, and any other monomer which forms a copolymer with carboxylic acids or derivatives. Although these copolymers can be prepared by direct polymerization of the various monomers, frequently they are more easily prepared by an after-reaction modification of an existing copolymer. Copolymers are conveniently identified in terms of their monomeric constituents. The names so applied refer to the molecular structure and are not limited to the polymers prepared by the copolymerization of the specified monomers.

The initial copolymers of anhydrides and another monomer can be converted to carboxyl-containing copolymers by reaction with water, and to ammonium, alkali and alkaline earth metal and alkylamine salts thereof by reaction with water, and to ammonium, alkali and alkaline earth metal and alkylamine salts thereof by reaction with alkali metal compounds, alkaline earth metal compounds, amines or ammonia. Other suitable derivatives of the above polymers include the alkyl or other esters and amides, alkyl amides, dialkyl amides, phenylalkyl amides or phenyl amides prepared by reacting carboxyl groups on the polymer chain with the selected amines or alkyl or phenylalkyl alcohol, as well as amino esters, amino amides, hydroxy amides and hydroxy esters, wherein the functional groups are separated by alkylene, phenyl, alkylene amine, alkylene oxide, phenylalkyl, phenylalkylphenyl, or alkylphenylalkyl or other aryl groups. Moieties bearing amine or amine salts including quaternary salt groups are conveniently formed by reaction of the carboxyl of their anhydride precursors, where applicable with polyfunctional amines such as dimethylaminoethanol, the former forming an amide linkage with the polymer, or in certain cases at higher temperatures forming an imide linkage with vicinal carboxyl, and the latter forming an ester linkage. Such pendant free amino groups can then be converted, if desired, to their simple or quaternary salts.

Polymers of the above type include the following classes of polymers, and their derivatives: ethylene/-maleic anhydride copolymers, isobutylene/maleic anhydride copolymer, 2-methyl-pentene-1/maleic anhydride copolymers, styrene/maleic anhydride copolymers, vinylacetate/maleic anhydride copolymers, α-methylstyrene/maleic anhydride copolymers, polymaleic anhydride polymers, polyacrylic anhydride polymers, polyacrylic acid polymers, octadecene-1/maleic anhydride copolymers, loweralkylaminoloweralkylimide of octadecene-1/maleic anhydride copolymers, aliphatic ester of ethylene/maleic anhydride copolymers, vinylalkylether/maleic anhydride copolymers, aliphatic methacrylate/methacrylamide, copolymers, aliphatic methacrylate/diloweralkylaminoloweralkyl methacrylate copolymers, loweralkylaminoloweralkylimide of styrene maleic anhydride copolymers and polymethacrylic acid polymers.

Individual examples of such polymers include ethylene/maleic anhydride copolymer, the disodium salt of isobutylene/maleic anhydride copolymer, the calcium salt of styrene/maleic anhydride copolymer, hydrolyzed propylene/maleic anhydride copolymer, the monopotassium salt of divinylether/maleic anhydride copolymer, hydrolyzed vinyl methyl ether/citraconic anhydride copolymer, half lauryl ester of octene-1/maleic anhydride copolymer, octadecene-1/maleic anhydride copolymer, ethylene/maleic acid copolymer, the dipotassium salt of isobutylene/maleic acid copolymer, the half amide half ammonium salt of isobutylene/maleic anhydride copolymer, ethylene/acrylic acid copolymer, ethylene/acrylic anhydride copolymer, half capryl ester of hexene-1/acrylic anhydride copolymer, ethylene/aconitic anhydride copolymer, half ethylamide of styrene/maleic anhydride copolymer, ethylene/fumaric acid copolymer, octylamide acid of ethylene/maleic anhydride copolymer, octadecylamide ammonium salt of vinylmethylether/maleic anhydride copolymer, dimethylaminopropylamide acid of divinylether/maleic anhydride copolymer, isobutylamide of vinyl acetate/maleic anhydride copolymer, methiodide quaternary derivative of N,N-dimethylaminoethylamide of polymaleic anhydride, octadecyl ester ammonium salt of ethylene/itaconic anhydride copolymers, butylamine half amide of hexene-1/chloromaleic anhydride copolymer, the partial diamide of ethylene/maleic anhydride copolymer, n-decylamide of decene-1/maleic anhydride copolymer, N,N-diethylaminopropylamide ammonium salt of isobutylene/maleic anhydride copolymer, dimethyl sulfate quaternary salt of dimethylaminoethylamide of polymaleic anhydride, the partial half hexylamide of vinylmethylether/maleic anhydride copolymer, the diammonium salt of ethylene/maleic anhydride copolymer, the monoamide acid of propylene/maleic anhydride copolymer, N-ethyl monoamide of divinylether/maleic anhydride copolymer, N-dodecyl monoamide of vinylmethylether/maleic anhydride copolymer, N,N-dimethylaminopropylimide of triacontene/maleic anhydride copolymer, N,N-dimethylaminopropyl monoamide of styrene/citraconic anhydride copolymer, n-butyl-monoamide of polymaleic anhydride, N,N-diethyl-monoamide ammonium salt of vinyl acetate/maleic anhydride copolymer, n-butylimide of ethylene/maleic anhydride copolymer, octadecylimide of polymaleic anhydride, N,N-dimethylaminopropylimide of styrene/maleic anhydride copolymer, dimethylsulfate quaternary salt of diethylaminopropylimide of divinylether/maleic anhydride copolymer, N,N-dimethylaminopropyl half amide of paramethyl styrene/maleic anhydride copolymer, methyliodide quaternary salt of dimethylaminohexyl half amide half ammonium salt of α-methylstyrene/maleic anhydride copolymer, N,N-diethylaminoethyl half amide half sodium salt of isobutylene/maleic anhydride copolymer, partial lauryl ester of ethylene/maleic anhydride copolymer, vinyl octadecyl ether/maleic anhydride copolymer, stearyl methacrylate/methacrylamide copolymer and stearyl methacrylate/N,N-dimethylaminoethyl methacrylate copolymer.

A particularly preferred class of polymers for use in the present invention are lipophilic polymers, that is, polymers which have a lipophilic grouping or groupings included therein. A lipophilic grouping or moiety typically contains 6 or more atom units and may be in any suitable form such as a polyalkylene or alkylene oxide containing 6 or more atom units or as an ester, amide or imide unit containing 6 or more atom units, for example, 6 to 30, carbon atoms formed by reaction of the carboxyl containing monomer with lipophilic amines or alcohols such as, for example, hexanol, octanol, octylamine, hexylamine, octadecanol, etc., and the like. Examples of such preferred polymers include the octadecylimide of polymaleic anhydride, the methyl iodide quaternary salt of dimethylaminohexyl half amide half ammonium salt of α-methylstyrene/maleic anhydride copolymer, dodecyl monoamide of vinylmethylether/maleic anhydride copolymer, the octadecyl ester ammonium salt of ethylene/itaconic anhydride copolymer, the decylamide of decene-1/maleic anhydride copolymer, octadecene-1/maleic anhydride copolymer, etc., and the like.

Pharmaceutically acceptable alkaline earth metals and alkali metals, such as calcium, magnesium and potassium are useful in preparing conveniently administered forms of the polyelectrolyte polymers of this invention. The salts of metals such as magnesium, aluminum, zinc, iron, barium and bismuth are also useful in the present invention.

Representative EMA-type carboxylic acid or anhydride-olefin polymers, especially maleic acid or anhydride-olefin polymers of the foregoing type are known, for example, from U.S. Pat. Nos. 2,378,629; 2,396,785; 3,157,595; and 3,340,680. Generally, the copolymers are prepared by reacting ethylene or other unsaturated monomer, or mixtures thereof, with the acid anhydride in the presence of a peroxide catalyst in an aliphatic or aromatic hydrocarbon solvent for the monomers but nonsolvent for the interpolymer formed. Suitable solvents include benzene, toluene, xylene, chlorinated benzene and the like. While benzoyl peroxide is usually the preferred catalyst, other peroxides such as acetyl peroxide, butyryl peroxide, ditertiary butyl peroxide, lauroyl peroxide and the like, or any of the numerous azo catalysts, are satisfactory since they are soluble in organic solvents. The copolymer typically contains from about 25 to about 75% (mole %) of the olefin and preferably contains substantially equimolar quantities of the olefin residue and the anhydride or acid residue; that is, a mole ratio of olefin to anhydride or acid in the range of from about 2:3 to about 3:2. Generally, the copolymer will have a degree of polymerization of 8 to 100,000 preferably about 100 to 5,000, and a molecular weight of about 3,000 to 1,000,000, preferably about 10,000 to 500,000. The properties of the polymer, such as molecular weight, for example, are regulated by proper choice of the catalyst and control of one or more of the variables such as ratio of reactants, temperature, and catalyst concentration or the addition of regulating chain transfer agents, such as diisopropyl benzene, propionic acid, alkyl aldehydes, or the like. Numerous of these polymers are commercially available.

Derivatives containing basic or cationic groups can be prepared by any convenient procedure. Representative derivatives of polymers employed in the present invention are known to the art, for example, from U.S. Pat. No. 3,398,092. One group of useful derivatives are those in which the carboxyl groups are partially replaced with basic or cationic bearing moieties. For example, useful derivatives are conveniently formed by reaction of the carboxyls with polyfunctional amines such as dimethylaminopropylamine or dialkylaminoalcohols such as dimethylaminoethanol, the former forming an amide linkage with the polymer, or in certain cases at higher temperatures forming an imide linkage with the vicinal carboxyls and the latter forming an ester linkage. Such pendant free amine groups can then be converted, if desired, to their simple or quaternary salts.

Imides of a starting carboxy or carboxylic acid anhydride containing polymer, e.g., EMA, are produced by:

(A) Heating a limiting amount of a secondary or tertiary aminoloweralkylamine with the anhydride or carboxyl-containing form of the polymer in a suitable solvent (e.g. Xylene) at a temperature of about 140°–150° C. until water is no longer given off. Such a reaction simultaneously results in formation of imide groups in proportion to the amount of amine added and in the reformation of anhydride groups for the remainder of the polymer units. In this manner, imide-polymer products are formed which possess imide linkages, the remaining carboxyl groups, when present, being in the anhydride form.

(B) Alternativly, a partial amide-polymer product may be converted to the partial imide polymer product by heating a partial amide-polymer product in vacuo at 140°–150° C. until water is no longer given off. Such an imide polymer product likewise possesses comparable proportions of imide and anhydride groups depending upon the number of amide groups originally contained in the starting partial amide-polymer product.

Partial secondary or tertiary aminoloweralkylamides of the starting carboxyl or carboxylic acid anhydride-containing polymer, e.g., EMA, are obtained by contacting the polymer with a limiting amount of the selected amine in suspension in a solvent such as benzene or hexane, resulting in formation of a partial amide-acid-anhydride derivative of the polymer, or a corresponding amide-carboxylate derivative thereof. The number of amide groups is dependent upon the quantity of the amine used as compared with the quantity of polymer employed.

Partial aminoester-polymer products are most conveniently prepared by heating at reflux temperatures overnight a limiting quantity of the selected amino-alcohol and carboxyl or carboxylic acid anhydride containing polymer, e.g., EMA, in a dry organic solvent such as toluene or dimethylformamide and with the optional use of an acidic or basic catalyst such as p-toluenesulfonic acid or sodium alkoxide. The resulting product contains ester groups, carboxylic acid groups and anhydride groups, the respective numbers of which are determined by the quantity of aminoalcohol used in the reaction compared to the amount of polymer employed and, in some cases, by the temperature at which the reaction is carried out.

Suitable blocking and unblocking of the amine moiety of the reactant employed in preparing amides, esters or imides may be effected when required. Residual, non-modified, polymer units may optionally be converted to neutral groups or units by attachment to the polymer molecule of compounds including alkylamines, aminoalcohols, and alcohols.

Alternatively, the cationic character of the polymer can be provided through incorporation of monomers which impart a basic or cationic character such as C-vinyl pyridines, vinyl amine, the several amino-substituted vinyl benzenes (or toluenes, etc.), amine-bearing acrylates (or methacrylates, etc.), vinyl imidazole, etc.

The invention will be understood more fully by reference to the following specific examples. It is understood that the examples are presented for the purpose of illustration only and are not intended as a limitation of the invention.

EXAMPLE 1

A group of 144 Columbian male chicks (one day old) was divided in 12 equal sub-groups. Each sub-group of 12 chicks was fed a basal diet and the supplement shown in Table 1 for a three-week period. Throughout the test period water was supplied ad libitum. The basal diet employed was designed to raise the level of blood cholesterol in the chicks to which it was fed. On conclusion of the feeding period the chicks were sacrificed and plasma cholesterol level was determined by the general procedure described in Chin, Chim. Acta. 10 381–84 (1964) by Levine and Zak. Fecal cholesterol and fecal lipid were also determined. In the test the copolymers of diets 2–10 and 12 are linear and the copolymer of diet 11 is crosslinked. The results are set forth in Table 1:

| Basal Diet | |
|---|---|
| Ingredient | % by Weight |
| Soybean Meal | 25.00 |
| Whole Egg (Powder) | 25.00 |
| Vitamin Supplement | 0.40 |
| Choline Chloride | 0.14 |
| Iodized Salt | 0.05 |
| Delamix | 0.10 |
| Dicalcium Phosphate | 2.00 |
| Calcium Carbonate | 1.00 |
| Vitamin A (10,000)u/g | 0.10 |
| Vitamin D (1,500)u/g | 0.008 |
| Alpha Cel | 3.00 |
| Cerelose | 42.752 |

The results of this test show that the polyelectrolyte polymers of the present invention are effective in lowering blood cholesterol and in increasing fat excretion.

TABLE 1

| Diet | Polymer | Level in Feed % by Weight | Plasma Cholesterol mg/100 ml. | Fecal Cholesterol % Dry Weight | Fecal Lipid % Dry Weight |
|---|---|---|---|---|---|
| 1 | None (Control) | — | 213 | 0.75 | 4.70 |
| 2 | Octadecene-1/Maleic Anhydride Copolymer | 0.5 | 183 | 1.06 | 6.9 |
| 3 | Octadecene-1/Maleic Anhydride Copolymer | 1.0 | 150 | 1.32 | 9.28 |
| 4 | Octadecene-1/Maleic Anhydride Copolymer | 2.0 | 125 | 1.38 | 7.74 |
| 5 | Octadecene-1/Maleic Anhydride Copolymer | 3.0 | 107 | 1.43 | 10.29 |
| 6 | N,N-Dimethylaminopropyl-imide of Octa- | | | | |

TABLE 1-continued

| Diet | Polymer | Level in Feed % by Weight | Plasma Cholesterol mg/100 ml. | Fecal Cholesterol % Dry Weight | Fecal Lipid % Dry Weight |
|---|---|---|---|---|---|
| | decene-1/Maleic Anhydride Copolymer | 3.0 | 114 | 1.58 | 24.7 |
| 7 | Partial Lauryl Ester of Ethylene/ Maleic Anhydride Copolymer | 3.0 | 149 | 0.64 | 7.4 |
| 8 | Vinyloctadecyl Ether/Maleic Anhydride Copolymer | 3.0 | 141 | 1.06 | 8.1 |
| 9 | Stearyl Methacrylate/Methacrylamide Copolymer | 3.0 | 136 | 1.32 | 9.8 |
| 10 | Stearyl Methacrylate/N,N-dimethylamino Ethyl Methacrylate Copolymer | 3.0 | 120 | 1.56 | 22.4 |
| 11 | N,N-Dimethylaminopropylimide of Styrene/Maleic Anhydride Copolymer | 3.0 | 107 | 1.53 | 20.3 |
| 12 | Octene-1/Maleic Anhydride Copolymer | 3.0 | 147 | 1.40 | 12.21 |

EXAMPLE 2

A group of 36 Vantress-Arbor Acre male chicks (one day old) was divided into three equal subgroups. Each subgroup of 12 chicks was fed the Basal Diet of Example 1 and 3.0% of the supplement shown in Table 2 for a three week period. Throughout the test period water was supplied ad libitum. On conclusion of the feeding period the chicks were sacrificed and plasma cholesterol level was determined by the procedure referred to in Example 1. In the test the copolymers of diet 14 and 15 were crosslinked. The results are set forth in Table 2.

TABLE 2

| DIET | POLYMER | PLASMA CHOLESTEROL mg/100 ml |
|---|---|---|
| 13 | None | 290.5 |
| 14 | Ethylene/maleic Anhydride | 204.8 |
| 15 | Ethylene/maleic Anhydride Hydrolyzed | 192.8 |

EXAMPLE 3

The procedure of Example 2 was repeated. The polymers used and the results obtained are given in Table 3.

TABLE 3

| DIET | POLYMER | PLASMA CHOLESTEROL mg/100 ml |
|---|---|---|
| 16 | None | 309 |
| 17 | Ethylene/maleic Anhydride (crosslinked) | 275 |
| 18 | Ethylene/maleic Anhydride Calcium Salt (crosslinked) | 255 |

EXAMPLE 4

The procedure of Example 1 is repeated in all essential details with the exception that the polymer is polymaleic anhydride to lower the blood cholesterol level of chicks.

EXAMPLE 5

The procedure of Example 1 is repeated in all essential details with the exception that the polymer is polyacrylic anhydride to lower the blood cholesterol level of the chicks.

EXAMPLE 6

The procedure of Example 1 is repeated in all essential details with the exception that the polymer is polyacrylic acid to lower the blood cholesterol of the chicks.

EXAMPLE 7

The procedure of Example 1 is repeated in all essential details with the exception that the polymer is polymethacrylic acid to lower the blood cholesterol level of the chicks.

EXAMPLE 8

Cattle having a high level of blood cholesterol are fed a daily ration containing from 0.01 to 5.0% of octadecene-1/maleic anhydride and the level of their blood cholesterol is lowered.

EXAMPLE 9

Heavyweight Hampshire hogs having a high level of blood cholesterol are fed a daily ration containing from 0.01 to 3.0% of N,N-dimethylaminopropylimide of octadecene-1/maleic anhydride copolymer and the level of their blood cholesterol is lowered.

EXAMPLE 10

Aged chimpanzees having a high level of blood cholesterol are fed a daily ration containing from 0.05 to 1.0% of octadecene-1/maleic anhydride copolymer and the level of their blood cholesterol is lowered.

EXAMPLE 11

This example shows the effectiveness of octadecene-1/maleic anhydride (substantially equimolar copolymer) in the method of the present invention. Twenty-four New Zealand white rabbits weighing an average of 2600 grams each were divided into three groups of equal number. The rabbits were fed ad libitum for five weeks a low cholesterol diet. The first group (control) was fed Purina Rabbit Chow brand rabbit feed supplemented with 2% animal tallow and 1% cellulose. The second group was fed the identical feed as the control with the exception that 1% octadecene-maleic anhydride was substituted for the 1% cellulose. The third group was fed the identical feed as the control with the exception that 1% CHOLESTYRAMINE, a crosslinked divinyl-benzene-polystyrene ion exchange resin containing quaternary ammonium groups was substituted for the 1% cellulose. On completion of the five week feeding period the animals were sacrificed and the following measurements were made: (1) plasma cholesterol, (2) plasma triglyceride, (3) liver cholesterol, and (4) liver fat. The measurements were averaged and are presented in Table 4. These results when considered as a whole indicate that higher α-olefin/maleic anhydride copolymers are effective in lowering blood lipids, i.e., in the treatment of hypercholesterolemia.

EXAMPLE 12

This example shows the effectiveness of octadecene-1/maleic anhydride (substantially equimolar copolymer) in the method of the present invention. Forty New Zealand white rabbits weighing an average of 2600 grams each were divided into five groups of equal number. The groups were fed ad libitum for five weeks a high cholesterol diet. The first group (control) was fed Purina Rabbit Chow brand rabbit feed supplemented with 2% animal tallow, 1% cellulose and 0.2% cholesterol. The second group was fed the identical feed as the control with the exception that 0.5% octadecene-maleic anhydride was substituted for 0.5% of the cellulose. The third group was fed the identical feed as the control with the exception that 1% octadecene maleic anhydride was substituted for the 1% cellulose. The fourth group was fed the identical feed as the control with the exception that 0.5% CHOLESTYRAMINE was substituted for 0.5% of the cellulose. The fifth group was fed the identical feed as the control with the exception that 1% CHOLESTYRAMINE was substituted for the 1% cellulose. Feces were collected during the final day of the test. On completion of the five-week feeding period the animals were sacrificed. The measurements performed in Example 11 above were carried out. Fecal fat was also measured. The measurements were averaged and are presented in Table 5.

EXAMPLE 13

This example shows the effectiveness of polymers useful in the present invention. Four hundred and sixty-eight one-day old chicks (Vantress-Arbor Acre Cockerels) were divided into thirteen groups of equal number. Each group of chicks was fed ad libitum for 21 days a high cholesterol diet of soybean meal, whole egg powder, minerals and vitamins. Cholesterol lowering additive in the amount indicated in Table 6 was added to the diet of groups 2-13. Group 1 served as a control. Feces were collected for a 24-hour period between days 19 and 20. On completion of the 21-day test the birds were sacrificed and the following measurements were made: (1) plasma cholesterol, (2) liver cholesterol, and (3) liver fat, as well as cholestrol and fat excretion. The measurements were averaged and are presented in Table 6. Fat excretion was increased.

EXAMPLE 14

This example shows the effectiveness of representative members of (1) a group of polymers which are copolymers of higher α-olefins (10-22 carbon atoms or more) and maleic acid or maleic anhydride and (2) a group of polymers which are copolymers of higher alkyl vinyl ethers (10-22 carbon atoms or more) and maleic acid or maleic anhydride. The maleic acid copolymers were prepared by hydrolysis of the corresponding maleic anhydride copolymers in 5% acetic acid in water at 50° C. for 24 hours followed by freeze drying.

Thirty-six female rabbits (1.5-2.0 kilograms each) were placed in individual cages. The rabbits were randomly divided into 12 groups (3 animals per group) for feeding purposes and fed ad libitum for three weeks high cholesterol diets. The first group (control) was fed a basal diet designed to induce hypercholesterolemia. The diet consisted of Purina Rabbit Chow brand rabbit feed supplemented with 2% animal tallow, 0.2% cholesterol and 1% cellulose. The other 11 groups were fed the identical basal diet as the control group with the exception that 1% of a copolymer useful in the present invention was substituted for the 1% cellulose. On completion of the three-week feeding period the animals were weighed and blood samples were taken. The samples were analyzed for cholesterol (Technicaon autoanalyzer). At the beginning of the test, a blood sample was taken from each animal (heart puncture) and analyzed for cholesterol. All results are presented in Table 7. The effectiveness of a tested compound is shown by comparing the final plasma cholesterol of the animals treated with the compound with the final plasma cholesterol of the control animals.

EXAMPLE 15

Three baboons were fed a high cholesterol diet for eight weeks. At the beginning of the fourth week of feeding, octadecene-1/maleic anhydride copolymer (0.5% by weight of the total diet) was added to the diet of two of the baboons and equal CHOLESTRYRAMINE, a crosslinked divinylbenzene-polystyrene ion exchange resin containing quaternary ammonium groups was added to the diet of the third baboon. In each of the three animals the blood cholesterol level was found to be lower at the end of the eighth week than at the end of the third week with the blood cholesterol level at the end of the eighth week being lower in the two animals fed the diet containing octadecene/maleic anhydride copolymer than in the animal fed the diet of CHOLESTYRAMINE.

Representative formulations embodying polymers within the scope of the present invention are:

| TABLET FORMULATION | | |
|---|---|---|
| The following formulation provides for the manufacture of 1,000 tablets: | | |
| | | GRAMS |
| (1) | Octadecene-1/maleic anhydride copolymer | 25 |
| (2) | Lactose | 181 |
| (3) | Corn Starch | 92 |
| (4) | Magnesium Stearate | 2 |

Thoroughly granulate a mixture of 72 grams of cornstarch and the lactose with a paste prepared by dissolving 20 grams of cornstarch in 100 ml of hot distilled water. Dry the resulting granulation at 40°-45° C. and pass it through a No. 16-mesh screen. To the dried, screened granulation add a blended mixture of the active ingredient (1) and the magnesium stearate. Thoroughly blend and then press into tablets of 300 mg. each.

| CAPSULE FORMULATION | | |
|---|---|---|
| The following formulation provides for the manufacture of 1,000 capsules: | | |
| | | GRAMS |
| (1) | N,N-dimethylaminopropylimide of octadecene-1/maleic anhydride copolymer | 25 |

CAPSULE FORMULATION

The following formulation provides for the manufacture of 1,000 capsules:

|     |                   | GRAMS |
| --- | ----------------- | ----- |
| (2) | Lactose           | 274   |
| (3) | Magnesium Stearate | 2    |

Mix active ingredient (1) with the lactose and blend in the magnesium stearate. Fill hard gelatin capsules with 300 mg. each of the blended mixture to produce capsules containing the active ingredient.

While the invention has been described with reference to particular embodiments thereof, it will be appreciated that modifications and variations are possible without departing from the invention.

TABLE 4

|         |                                | PLASMA | | LIVER | |
|---------|--------------------------------|--------|---|-------|---|
|         |                                | Cholesterol *mg % | Triglyceride *mg % | Cholesterol % of wet weight | Fat % of wet weight |
| Group 1 | (Control)                      | 52  | 82  | .38 | 6.89 |
| Group 2 | (1% Octadecene-maleic Anhydride) | 43  | 87  | .36 | 5.12 |
| Group 3 | (1% CHOLESTYRAMINE)            | 74  | 110 | .39 | 5.69 |

*mg per 100 cc plasma

TABLE 5

|         |                                 | PLASMA | | LIVER | | FECES |
|---------|---------------------------------|--------|---|-------|---|-------|
|         |                                 | Cholesterol *mg % | Triglyceride *mg % | Cholesterol % of wet weight | Fat % of wet weight | Fat % of dry wt. |
| Group 1 | (Control)                       | 672 | 106 | .92 | 7.80 | 4.51 |
| Group 2 | (0.5% Octadecene-maleic anhydride) | 186 | 113 | .47 | 5.98 | 6.03 |
| Group 3 | (1.0% Octadecene-maleic anhydride) | 89  | 56  | .41 | 5.80 | 6.29 |
| Group 4 | (0.5% CHOLESTYRAMINE)           | 356 | 68  | .79 | 7.36 | 7.12 |
| Group 5 | (1.0% CHOLESTYRAMINE)           | 310 | 105 | .74 | 7.18 | 6.04 |

*mg per 100 cc of plasma.

TABLE 6

|          |                                                                    | Weight Grams | Feed Consumed Grams | Plasma Cholesterol mg % | Liver Cholesterol % wet wt. | Liver Fat % wet wt. | Excreta Cholesterol % dry wt. | Excreta Fat % dry wt. |
|----------|--------------------------------------------------------------------|--------------|----------------------|--------------------------|------------------------------|---------------------|-------------------------------|------------------------|
| Group 1  | (control)                                                          | 328 | 472 | 257 | 2.58 | 10.7 | 0.46 | 8.2  |
| Group 2  | (Octadecene-maleic anhydride) (0.6%)                               | 360 | 483 | 250 | 1.26 | 8.9  | 0.97 | 6.3  |
| Group 3  | (Octadecene-maleic anhydride) (1.2%)                               | 338 | 509 | 236 | 0.57 | 7.6  | 1.03 | 10.1 |
| Group 4  | (CHOLESTYRAMINE) (0.6%)                                            | 364 | 480 | 181 | 0.50 | 7.6  | 1.09 | 11.9 |
| Group 5  | (CHOLESTYRAMINE) (1.2%)                                            | 331 | 428 | 154 | 0.45 | 7.7  | 1.12 | 11.4 |
| Group 6  | (Octadecene-maleic anhydride dimethylaminopropylimide-100% derivative) (0.6%) | 354 | 491 | 226 | 0.89 | 8.2  | 0.83 | 11.2 |
| Group 7  | (Octadecene-maleic anhydride dimethylaminopropylimide-67% derivative) (0.6%)  | 315 | 456 | 258 | —    | —    | 0.65 | 12.8 |
| Group 8  | (Stearylmethacrylate/dimethyl aminoethylmethacrylate) (0.6%)       | 233 | 395 | 206 | 0.57 | 7.2  | 1.01 | 17   |
| Group 9  | (Stearylmethacrylate/dimethylaminoethylmethacrylate) (0.6%)        | 370 | 501 | 262 | —    | —    | 0.80 | 14.1 |
| Group 10 | (Vinyloctadecyl ether/maleic anhydride) (0.6%)                     | 361 | 463 | 242 | 0.87 | 7.9  | 1.11 | 12.0 |
| Group 11 | (Vinyloctadecyl ether/maleic anhydride) (0.6%)                     | 360 | 514 | 298 | —    | —    | 0.97 | 9.5  |
| Group 12 | (Stearyl methacrylate/methacrylic acid (0.6%)                      | 358 | 439 | 282 | —    | —    | 0.73 | 9.5  |
| Group 13 | (Stearyl methacrylate/methacrylic acid)                            | 369 | 455 | 274 | —    | —    | 0.84 | 9.5  |

TABLE 6-continued

| | Weight Grams | Feed Consumed Grams | Plasma Cholesterol mg % | Liver Cholesterol % wet wt. | Liver Fat % wet wt. | Excreta Cholesterol % dry wt. | Excreta Fat % dry wt. |
|---|---|---|---|---|---|---|---|
| (0.6%) | | | | | | | |

TABLE 7

| Polymer | Weight Gain in Grams For 3 Week Period (Average) | Plasma Cholesterol Initial mg.%* (Average) | Plasma Cholesterol Final mg.%* (Average) |
|---|---|---|---|
| Group 1 (Control) | 546 | 53 | 377 |
| 2 Octadecene/maleic anhydride (2:3)[1] | 461 | 51 | 117 |
| 3 Octadecene/maleic acid (2:3) | 487 | 123 | 84 |
| 4 Octadecene/maleic anhydride (1:1) | 436[2] | 147[2] | 70[2] |
| 5 Octadecene/maleic acid (1:1) | 288 | 61 | 112 |
| 6 Decene/maleic anhydride (1:1) | 228 | 67 | 153 |
| 7 Decene/maleic acid (1:1) | 320 | 78 | 117 |
| 8 Octadecyl vinyl ether/maleic anhydride | 460 | 91 | 162 |
| 9 Octadecyl vinyl ether/maleic acid | 279[3] | 64[3] | 344[3] |
| 10 Dodecyl vinyl ether/maleic anhydride (1:1) | 365 | 70 | 260 |
| 11 Dodecyl vinyl ether/maleic acid (1:1) | 538 | 60 | 103 |
| 12 Hexene/maleic anhydride (1:1) | 670 | 60[4] | 472[4] |

*mg. per 100 cc of plasma
[1] mole ratio of α-olefin to anhydride
[2] 1 animal died of diarrhea during test (average of 2 animals)
[3] 1 animal suffered severe weight loss due to diarrhea during test (average of 2 animals)
[4] 2 animals suffered severe weight loss due to diarrhea during test.

It is preferred to utilize pancreatic lipase inhibiting polymers herein. Polymers are considered lipase inhibiting herein if they cause at least 50% inhibition in the hydrolysis rate of olive oil emulsion when employed at concentrations no greater than 15% by weight of the olive oil in saline media at pH circa 6.8 in the presence of taurocholic acid. The determination can be made with an amount of pancreatic lipase equal to 2 mg per gram of olive oil, with each activity of 71.1 units per mg., and titrating the hydrolyzed fatty acid with 0.01 N NaOH. A unit of lipase activity is that which hydrolyzes 1 microequivalent of fatty acid from triglyceride substrate in one hour at pH of 7.4 at 37° C.

The polymers utilized herein have particular functional characteristics which are apparently responsible for effectiveness. The polymers are believed to be effective because of their involvement in fat breakdown and transportation and absorption of fat and related materials. The useful polymers in general have surfactant characteristics, and can be termed polymeric surfactants, with the term "surfactant" referring to materials having a tendency to concentrate at the surface of an aqueous solution and to alter its surface properties. Surfactants in general have hydrophobic groups, and this appears to be true of the polymeric surfactants utilized herein. The polymers utilized herein usually have some hydrocarbon or similar moiety, and a hydrophilic carboxyl group or derivative. It appears that the efficiency of the polymers is affected by the size and character of the hydrophobic groups. Lipophilic groups often have chains similar in length or properties to those of natural fats, and can have, for example, hydrocarbon chains of 6 or 8 or so carbon atoms up to 22 or 24 or more carbon atoms. In the event oxygen or other hetero atoms are included, as from polymerization of a vinyl ether, the chain lengths may vary somewhat but can be selected to have characteristics like the aforesaid hydrocarbon chains. There generally is no reason to use hydrophobic groups with more than the suggested range of carbon atoms and such often are not readily available, but groupings of appropriate lipophilic character can be used containing up to 30 or more carbon atoms. There is some indication that groupings tend to decline in or lose lipophilic character as extremely long chain lengths are reached and it may be advisable to avoid such if the advantages of lipophilic character are to prevail. Polymers from higher molecular weight olefins trend toward a waxy character as molecular weight is increased, in contrast to the non-waxy character of polymers from lower molecular weight range olefins.

The polymeric surfactants used herein contain hydrophilic groups which are generally the carboxyl group or a derivative thereof. Appropriate hydrophilic character in use can be supplied by using polymers with free carboxyl or anhydride groups, so frequently such groups are utilized along with other partial derivative groups. However polymeric surfactants having various carboxyl derivatives as discussed herein can be used. Such derivatives can involve introduction of basic amine and positively-charged quaternary amine salt groups. The carboxyl group can, of course, also be utilized to introduce other hydrophobic groups, as by esterification with a long hydrocarbon chain alcohol wherein the hydrocarbon chain supplies hydrophobic character, and partial esters of carboxyl containing polymers described herein can be used in such embodiment or otherwise.

Further description of polymers considered suitable for use herein includes copolymers of vinyl ether with maleic acid or anhydride or appropriate derivatives, e.g., vinyl alkyl ethers with 8, 10, 12, 16 or 18 carbon atoms in the alkyl group, copolymers of vinyl ether with other unsaturated acids or appropriate derivatives, e.g., of acrylic acid, methacrylic acid, aconitic acid, itaconic acid, crotonic acid or citraconic acid, with for example the number of carbon atoms in the vinyl ether as stated for the maleic copolymers, with an alkyl of 12 carbon atoms being a convenient choice from a range of 8 to 20 or so; copolymers of olefinic hydrocarbons, such as of about 8 or 10 to about 18 or 22 carbon atoms with acrylic or methacrylic acids, although it may be necessary to use some special expedients to obtain such polymers, such as copolymerization of the olefin with acrylamide, followed by hydrolysis; copolymers of vinyl esters with unsaturated carboxylic acids, e.g., maleic acid or anhydride, acrylic acid, aconitic acid, itaconic acid, crotonic acid, citraconic acid, etc., with the ester carboxylate moiety having a number of carbon atoms in the range stated above for alkyl groups in copolymers of vinyl ethers with such acids, with vinyl esters of a C-12 carboxylic acid, or vinyl stearate being convenient choices; and long chain partial esters of the aforementioned unsaturated carboxylic acids, with the esterifying groups having a number of carbon atoms as in the aforementioned alkyl groups, e.g., stearyl methacrylate/methacrylic acid copolymer, stearyl acrylate/acrylic acid copolymer, or such variations as stearyl methacrylate/acrylic acid copolymer and the partial lauryl ester of ethylene/maleic acid copolymer.

The present invention provides pharmaceutical compositions containing the described polymers and pharmaceutically acceptable carriers therefor. Thus any of the polymers disclosed as effective herein, either generically or specifically, can be combined with carriers and used for administration in convenient dosage forms. Such pharmaceutical composition can include various carriers and additives as disclosed herein and can include various sweetening or flavoring agents to improve palatability. Also appropriate purification or sterilization procedures can be employed to provide a potable or sterile pharmaceutical composition fit for human consumption. The preparation procedures can include polymer isolation and purification procedures to insure standard uniform composition and physical form within specified tolerances in order to provide uniform quality, strength, effectiveness, and other properties, as well as procedures to insure food grade purity.

The administration of the various unsaturated acid, anhydride and derivative polymers and copolymers as taught herein is advantageous in providing a weight control method in animal bodies in need of such control. The method is useful regardless of whether the subjects involved also have problems of elevated blood cholesterol, triglycerides or lipids in general. However in some cases it may be useful in treating a combination of such manifestations by utilizing polymers suitable for influencing all.

The agents used in the present invention are intended to have their primary effect upon the fatty content of the diet, that is food requiring digestion caused by pancreatic lipase for absorption into the bloodstream. Thus it is contemplated as useful in conjunction with a diet containing such food. It may be particularly useful in situations involving a high fat diet where a restricted diet is impractical or unacceptable. However, the agents will also be useful when used in conjunction with a restricted diet, making such a diet more palatable by increasing the permitted caloric intake, particularly with respect to fat content. One mode of use involves limiting caloric intake from starch, sugars, etc. by dietary restrictions, while relying upon the polymeric agents as described herein to control fat utilization. In some cases a rather extreme combination of dietary restriction and administration of polymeric agents may be needed, but in general it will be appropriate to have regulation such as to have adequate nutrition together with the desired degree of weight control.

There may be advantage in having effect primarily on utilization of fatty foods. While interference with utilization of starches, sugars, etc., would also reduce caloric uptake, the presence and excretion of such undigested materials might present problems. Thus a more limited effect which still contributes to weight control may be advantageous.

Tests were conducted to determine lipase inhibition capability of various polymers. In vitro tests have been used in which the effect of polymers on lipolysis has been determined, generally by measuring the effect on lipolysis rate. Inhibition of the lipolysis rate is significant, as in an animal digestive system, there is only limited time for digestive enzymes to act upon food in the alimentary tract and dietary fats must be broken down for them to be absorbed.

The general materials and procedures for in vitro lipolysis studies were as follows:

A reaction vessel with constant temperature bath (37° C.) was employed with nitrogen blanket to exclude carbon dioxide, and a magnetic stirrer was employed. Automatic titration equipment was employed. Materials were as follows.

Pancreatic lipase (triacylglycerol lipase), E.C. No. 3.1.1.3, Type II, Crude from hog pancreas. Sigma Chemical Co., St. Louis, Mo.

Lipase activity was 71.1 units/mg (solids) with olive oil substrate. One unit is that which hydrolyzes 1.0 microequivalents of fatty acid from triglyceride substrate in one hour at pH of 7.4 and 37°.

Note: Crude lipase was used for experiments involving the presence of bile acids. This product contains a coenzyme which specifically overcomes inhibition of the bile acids and shifts the optimum pH of the lipase from 8.1 to 6.9. If a purified lipase were to be used, it would require concurrent addition of cofactor.

Olive oil substrate, 50% stabilized aqueous emulsion, Sigma Chemical Co., Stock No. 800-1.

Copolymers of $\alpha$-olefins and maleic anhydride (acid) and their amine derivatives were synthesized by conventional methods. They were employed in these studies as 0.5–1.0% aqueous solutions adjusted to pH 6.8.

The assays, which were run at pH of either 6.8 or 8.1, were generally carried out with reagents and procedures as follows:

| | Quantity per Assay | Concentration in Reaction Mix |
|---|---|---|
| Olive oil emulsion (50%) | 2 ml | 46 mM/l |
| Calcium chloride (0.075 M) | 2 ml | 5.4 mM/l |
| Sodium chloride (3 M) | 4 ml | 428 mM/l |
| | or 1.4 ml* | 150 mM/l* |
| Taurocholic acid (6.8%) | 10 ml* | 50 mM/l* |
| | or 0 ml | 0 mM/l |
| Water | adjust final volume to 28 ml | |
| pH | 6.8* or 8.1 | |
| Lipase | 2 mg | 71 mg/l |
| Copolymer | Designated amount of aqueous solution | |

*Representative of physiological conditions in intestinal lumen.

All reagents except enzyme were added to the reaction vessel maintained in a water bath at 37° C.[(1)] The magnetically-stirred reaction was blanketed with nitrogen during the titration. The solution was adjusted to the desired pH with 0.1 N HCl or 0.1 N NaOH. When the pH was stabilized, enzyme was added. The reaction was followed by titration of liberated fatty acid with 0.01 N NaOH and was recorded on the titrograph.

[(1)] In designated cases, the substrate, water, salts, taurocholate and polymeric inhibitor were pre-mixed and sonicated for 15 minutes prior to conducting the enzyme reaction.

To evaluate inhibition of the enzyme by the copolymers, a selected quantity of polymer solution was substituted for an equivalent volume of water in the basic reaction media.

Pancreatic lipase (E.C. No. 3.1.1.3) was prepared as a 1% solution in 0.005 M. calcium chloride. The pH was adjusted to 6.8 or 8.1 depending on the condition being tested. This solution (200 μl) was added to the 28 ml. content of the reaction vessel.

EXAMPLE 16

A series of copolymers of maleic anhydride and α-olefins ranging from $C_2$ through $C_{22}$ alkenes were evaluated as inhibitors at pH 8.1, utilizing the polymers at a level of 11% by weight of substrate (olive oil). All of the polymers inhibited the lipase to some extent, but the $C_6$ and $C_8$ olefin polymers were the most effective, as shown by the data at two different salt concentrations. The salt concentration did not significantly alter the rate of attack. The degree of inhibition was fairly strong for all the polymers from olefin of 6 or more carbon atoms. The results are reported in Tables 8 and 9 below, as velocity of the lipolysis $\times 10^3$, in terms of milliequivalents fatty acid liberated per minute.

Table 8

| Lipase Inhibition pH 8.1; 428 mM NaCl | |
|---|---|
| alkene/maleic | $V \times 10^3$ meq. FA/Min. |
| no polymer | 10.8 |
| $C_2$ | 6.5 |
| $C_3$ | 2.7 |
| $C_4$ | 3.3 |
| $C_6$ | 0.0 |
| $C_8$ | 0.45 |
| $C_{10}$ | 1.2 |
| $C_{14}$ | 1.2 |
| $C_{18}$ | 1.5 |
| $C_{18}$ (low m.w.) | 0.2 |

Table 9

| Lipase Inhibition pH 8.1; 150 mM NaCl | |
|---|---|
| alkene/maleic | $V \times 10^3$ meq. FA/Min. |
| no polymer | 10.4 |
| $C_2$ | 4.7 |
| $C_3$ | 3.0 |
| $C_4$ | 3.0 |
| $C_6$ | 0.03 |
| $C_8$ | 0.30 |
| $C_{10}$ | 1.90 |
| $C_{14}$ | 1.10 |
| $C_{18}$ | 1.20 |
| $C_{18}$ (low m.w.) | 0.4 |

With an octadecene copolymer, the low m.v. species appeared to be a somewhat better inhibitor, although the effect was not as pronounced as that of the hydrocarbon side chain resulting from the alkene used. The low molecular weight octadecene copolymer had a molecular weight of about 2700 compared to the usual 50,000 or so. In these and other tests herein involving maleic anhydride moieties, the anhydride is converted to the acid or salt form, depending on Ph, when utilized in aqueous media.

EXAMPLE 17

Enzyme action was assayed under conditions approximately those of the gut lumen employing salinity of 150 mM NaCl, utilizing bile acids as represented by taurocholic acid (50 mM) and a pH of 6.8. For comparison, a higher salt concentration was also studied. Crude pancreatic lipase was utilized in order to insure presence of enzyme cofactor which overcomes inhibition by bile acid and shifts the optimum pH for lipase enzyme activity from 8.1 to 6.8. A series of α-olefin maleic acid copolymers, with alkene olefin variation from $C_2$ to $C_{22}$ were studied, with results as reported below in Tables 10 and 11. It can be seen that polymers from $C_8$ olefin are very strong inhibitors, while others in the $C_2$ to $C_{12}$-$C_{14}$ or so range produce up to about 50% inhibition; with stronger inhibition at higher saline concentrations. A low molecular weight octadecene/maleic copolymer was a fairly effective inhibitor.

Table 10

| Lipase Inhibition pH 6.8; 150 mM NaCl | |
|---|---|
| alkene/maleic | $V \times 10^3$ meq. FA/Min. |
| no polymer | 5.5 |
| $C_2$ | 2.8 |
| $C_3$ | 2.5 |
| $C_4$ | 4.3 |
| $C_6$ | 2.9 |
| $C_8$ | 1.0 |
| $C_{10}$ | 2.5 |
| $C_{14}$ | 3.7 |
| $C_{18}$ | 4.9 |
| $C_{18}$ (low m.w.) | 3.3 |

Table 11

| Lipase Inhibition pH 6.8; 428 mM NaCl | |
|---|---|
| alkene/maleic | $V \times 10^3$ meq. FA/Min. |
| no polymer | 6.5 |
| $C_2$ | 3.4 |
| $C_3$ | 3.0 |
| $C_4$ | 5.3 |
| $C_6$ | 3.4 |
| $C_8$ | 0.0 |
| $C_{10}$ | 0.9 |
| $C_{14}$ | 2.5 |
| $C_{18}$ | 4.5 |
| $C_{22}$ | 5.5 |
| $C_{18}$ (low m.w.) | 3.2 |

It may be noted that in the alkene/maleic and series, the $C_6$ and $C_8$ polymers appear to be superior lipase inhibitors, even though comparatively poor for cholesterol control, while the $C_{18}$ is comparatively poor for lipase control even though a preferred cholesterol control agent.

EXAMPLE 18

Inhibition produced by varying concentration of octene-1/maleic acid copolymer was studied with results as reported below. At pH 6.8 a more than 50% inhibition was obtainable at a polymer concentration of 3% based on substrate. Results are reported in Tables 12 and 13 below.

Table 12

| Lipase Inhibition: Octene/Maleic Copolymer pH 6.8; 150 mM NaCl | | |
|---|---|---|
| Concentration | | |
| g. polymer/ ml substrate | g. polymer/ g. substrate | $V \times 10^3$ meq. FA/min. |
| 0.00 | 0.00 | 4.7 |
| 0.01 | 0.011 | 4.6 |
| 0.02 | 0.022 | 4.4 |
| 0.03 | 0.033 | 1.2 |
| 0.04 | 0.044 | 0.5 |
| 0.06 | 0.066 | 0.0 |
| 0.08 | 0.088 | 0.0 |
| 0.10 | 0.110 | 0.0 |

Table 13

Lipase Inhibition:
Octene/Maleic Copolymer
pH 8.1; 150 mM NaCl

| Concentration | | |
|---|---|---|
| g. polymer/ ml substrate | g. polymer/ g. substrate | $V \times 10^3$ meq. FA/min. |
| 0.000 | | 6.5 |
| 0.005 | .0055 | 3.6 |
| 0.010 | .011 | 3.9 |
| 0.015 | .0155 | 1.9 |
| 0.02 | .022 | 1.6 |
| 0.04 | .044 | 1.6 |
| 0.08 | .088 | 1.3 |
| 0.10 | .110 | 0.7 |

EXAMPLE 19

Dimethylaminopropylimide derivatives of olefin/maleic copolymer, and methyl iodide quaternary salts thereof, were assayed for inhibition effect, at varying polymer concentrations, 150 millimoles NaCl, and pH 6.8, with results as reported below in Tables 14 and 15.

Table 14

Lipase Inhibition
Dimethylaminopropylimides of Alkene/maleic Polymers
(pH 6.8; 150 mM NaCl)

| Alkene in Polymer | Polymer Conc. mg/ml $\times 10^2$ | Polymer Conc. mg/g. substrate | Rate of Enzyme Reaction (meq. F.A./ min $\times 10^3$) |
|---|---|---|---|
| Octene | 0 | 0 | 4.5 |
| | 3.6 | 1.1 | 5.4 |
| | 5.4 | 1.6 | 4.3 |
| | 7.1 | 2.2 | 0.5 |
| | 8.9 | 2.7 | 0.7 |
| | 12.5 | 3.8 | 0.7 |
| | 17.9 | 5.5 | 0.1 |
| Dodecene | 0 | 0 | 4.5 |
| | 3.6 | 1.1 | 4.9 |
| | 5.4 | 1.6 | 5.4 |
| | 7.1 | 2.2 | 5.0 |
| | 8.9 | 2.7 | 2.1 |
| | 12.5 | 3.8 | 0.1 |
| | 17.9 | 5.5 | 0.1 |
| Octadecene | 0 | 0 | 4.5 |
| | 5.4 | 1.6 | 5.0 |
| | 8.9 | 2.7 | 2.9 |
| | 12.5 | 3.8 | 0.0 |
| | 17.9 | 5.5 | 0.0 |

Table 15

Lipase Inhibition
Methyl Iodide Salts of
Dimethylaminopropylimides
of Alkene/maleic Polymers
(pH 6.8; 150 mM NaCl)

| Alkene in Polymer | Polymer Conc. mg/ml. $\times 10^2$ | Polymer Conc. mg/g. substrate | Rate of Enzyme Reaction (meq. F.A./ min. $\times 10^3$) |
|---|---|---|---|
| Octene | 0 | 0 | 4.5 |
| | 1.8 | 0.5 | 5.4 |
| | 3.6 | 1.1 | 5.1 |
| | 5.4 | 1.6 | 1.3 |
| | 8.9 | 2.7 | 1.3 |
| | 12.5 | 3.8 | 0.3 |
| | 17.9 | 5.5 | 0.5 |
| Dodecene | 0 | 0 | 4.5 |
| | 3.6 | 1.1 | 5.0 |
| | 5.4 | 1.6 | 0.3 |
| | 7.1 | 2.2 | 0 |
| Octadecene | 0 | 0 | 4.5 |
| | 3.6 | 1.1 | 5.5 |
| | 7.1 | 2.2 | 4.5 |
| | 8.9 | 2.7 | 0 |
| | 10.7 | 3.3 | 0 |
| | 17.9 | 5.5 | 0 |

EXAMPLE 20

Utilizing the $C_{18}\alpha$-olefin/maleic copolymer at a level of 11% by weight based on the olive oil substrate, and at pH 8.1 and 426 mM salt, a 70.6% inhibition was obtained. Variation of the substrate concentration then gave results as reported in Table No. 17 below, from which a Linweaver-Burk plot may be drawn. Variation of the inhibitor concentration permits construction of additional curves, with slopes increasing with inhibitor concentration, but having a common intercept on the Y axis. The inhibition constant was calculated as $K_I = 8.05 \times 10^{-2}$ mg/ml. These results suggest a competitive inhibition mechanism, with copolymer competing with normal substrate for enzyme binding sites.

Table 16

C-18 Olefin/maleic Copolymer; 4 mg./ml.

| Olive Oil Concentrate [S] $\times 10^3$ (mg/ml) | [1/S] $\times 10^{-3}$ (ml/mg) | 1/V $\times 10^{-3}$ (min/meq FFA) |
|---|---|---|
| 13.1 | .076 | 1.087 |
| 17.5 | .057 | .578 |
| 26.25 | .038 | .476 |
| 35.0 | .029 | .411 |
| 70.0 | .014 | .323 |

Table 17

No Polymer

| Olive Oil Concentrate [S] $\times 10^3$ (mg/ml) | [1/S] $\times 10^{-3}$ (ml/mg) | 1/V $\times 10^{-3}$ (min/meq FFA) |
|---|---|---|
| 1.75 | .571 | .233 |
| 3.50 | .286 | .172 |
| 5.25 | .191 | .149 |
| 8.75 | .114 | .133 |

EXAMPLE 21

Enzyme assays in accord with the general procedures above were conducted to obtain data appropriate for Linweaver-Burk plots, based on the recriprocal of the lipolysis rate and the reciprocal of the substrate concentration. The polymers utilized were the imide derivatives formed from dimethylaminopropylamine and $C_8$- and C-18 olefin/maleic anhydride copolymers respectively, and the methyl iodide salts of such copolymers. The data is reported in Table 18 below.

Table 18
Lipolysis at Varying Substrate Concentration

| | S × 10³ (mg/ml) | 1/S × 10⁻³ | V × 10³ (meq F.A./min × 10³) | 1/V × 10⁻³ |
|---|---|---|---|---|
| (1) Enzyme | 1.6 | 0.615 | 3.1 | 0.323 |
| No Inhibitor | 3.3 | 0.308 | 3.4 | 0.294 |
| | 4.9 | 0.205 | 3.3 | 0.303 |
| | 6.5 | 0.154 | 2.8 | 0.357 |
| | 9.8 | 0.103 | 4.0 | 0.250 |
| | 16.3 | 0.062 | 4.4 | 0.227 |
| (2) C₈ Copolymer- | 9.8 | 0.102 | 0.2 | 5.000 |
| DMAPA Imide | 16.3 | 0.062 | 1.1 | 0.909 |
| | 32.5 | 0.031 | 2.2 | 0.455 |
| | 48.8 | 0.021 | 3.9 | 0.256 |
| | 65.0 | 0.015 | 3.4 | 0.294 |
| (3) C₁₈ Copolymer | 13.0 | 0.077 | 0.9 | 1.111 |
| DMAPA Imide | 14.6 | 0.068 | 0.9 | 1.111 |
| (0.0536 mg/ml) | 16.3 | 0.062 | 2.0 | 0.500 |
| | 32.5 | 0.031 | 5.1 | 0.196 |
| | 48.8 | 0.021 | 4.2 | 0.238 |
| | 65.0 | 0.015 | 3.9 | 0.256 |
| (4) C₈ Copolymer | 9.8 | 0.102 | 0.9 | 1.111 |
| DMAPA Imide CH₃⁺I⁻ | 16.3 | 0.062 | 2.2 | 0.455 |
| (0.0357 mg/ml) | 32.5 | 0.031 | 5.4 | 0.185 |
| | 48.8 | 0.021 | 4.6 | 0.217 |
| | 65.0 | 0.015 | 4.3 | 0.233 |
| | 81.3 | 0.012 | 4.1 | 0.244 |
| (5) C₁₈ Copolymer | 3.25 | .308 | 1.1 | .909 |
| DMAPAI CH₃⁺I⁻ | 4.88 | .205 | 1.7 | .588 |
| | 6.5 | .154 | 3.6 | .278 |
| | 9.75 | .103 | 4.5 | .222 |
| (0.0179 mg/ml) | 3 | .077 | 5.4 | .185 |
| | 16.25 | .062 | 4.5 | .222 |
| (6) C₁₈ Copolymer | 3.25 | .308 | 0.0 | α |
| DMAPAI CH₃⁺I⁻ | 8.13 | .123 | 0.0 | α |
| | 8.93 | .112 | 1.3 | .769 |
| (0.0357 mg/ml.) | 9.75 | .103 | 1.8 | .556 |
| | 10.6 | .094 | 2.5 | .400 |
| | 1.38 | .088 | 4.9 | .204 |
| | 13.0 | .077 | 4.2 | .238 |
| | 14.63 | .068 | 5.2 | .192 |
| | 16.25 | .062 | 4.8 | .208 |
| | 32.5 | .031 | 4.8 | .208 |
| | 48.75 | .021 | 4.1 | .244 |
| | 65 | .015 | 3.5 | .286 |

While the above data can be plotted in approximately as straight lines to give plots having general characteristics of a competitive inhibition, there is an anomalous region in the inhibitor to substrate ratio around 1/1000.—Inhibition constants, $K_I$, for the copolymers calculate as follows.

| | |
|---|---|
| C₈ copolymer, DMAPA Imide | $2.49 \times 10^{-3}$ mg/ml. |
| C₁₈ copolymer DMAPA Imide | $1.74 \times 10^{-3}$ mg/ml. |
| C₈ copolymer DMAPA Imide, Quaternary methyl iodide salt | $2.1 \times 10^{-3}$ mg/ml. |
| C₁₈ copolymer DMAPA Imide, Quaternary methyl iodide salt | $1.64 \times 10^{-3}$ (at 0.0357 mg/ml). |
| C₁₈ copolymer DMAPA Imide, Quaternary methyl iodide salt | $2.92 \times 10^{-3}$ (at 0.0179 mg/ml). |

It is contemplated that the lipase inhibition function of the polymers as utilized herein may involve use of much lower amounts of polymer than ordinarily provided for other purposes. It may be that a small amount of suitable polymer may have a very pronounced effect by lipase inhibition, compared to that obtained by mere physical effects of polymers in interfering with fat assimilation. For example, dosages of less than 0.1% by weight of food intake, even down to 0.005% or lower or daily dosages no greater than one gram per day, may be found suitable with the polymers utilized herein. Accordingly, the unit dosage forms may be very small and a dosage regime more acceptable than is the case with, for example, some of the agents presently widely used for controlling blood cholesterol levels.

Lipase inhibiting activity of polymers as described herein has been found to be particularly enhanced in those polymers of cationic character. Cationic polymers are those polyelectrolyte polymers having positive charges when dissolved or suspended in aqueous media. The cationic polymers for use herein will suitably have such positive charges when dissolved or suspended under conditions for use at low pH and up through pH of 8 or so or conditions under which lipase activity is relevant.

As a practical matter to achieve the advantages of ionic groups the polymers should be soluble and therefore should not be cross-linked.

Soluble polymers are capable of dissolving in aqueous or fatty media. By dissolving is meant that the molecules are dispersed rather than present as particles of substantial size or material swollen by liquid, such as might occur with cross-linked polymeric products.

In order to be assured of cationic character it is desirable to employ polymers with a high concentration of carbonic groups under conditions of use, which may well be about pH 6.8 in the gut lumen. Polymers having a polymeric $pK_a$ no less than about 6 will have suitable cationic groups.

The $pK_a$ of a polymer is the negative log of the hydrogen ion concentration (moles/liter) at which it is 50% protonated. It can be determined for example, by potentiometric determination with hydrochloric acid titration, in water or salt solution, suitably in 0.15 N–0.5 N saline, or specifically at 0.15 N to correspond to physiological conditions. For example, the dimethylaminopropyl imide of α-octadecene/maleic acid or ethylene/maleic acid copolymers has a $pK_a$ of 8.25 and at pH 6.5–7 or lower is 90% to 100% protonated. Quaternary ammonium salts are completely ionized at any pH and therefore polymeric agents with quaternary ammonium moieties will be effective cationic agents for use herein aside from any determination of $pK_a$.

The cationic character of the agents herein can be provided by any groups in the polymer which ionize to give positive charges, but is most often provided by nitrogen groups, as in amine or quaternary ammonium groups. Such groups can ordinarily serve also as hydrophilic groups, or can be present along with some carboxyl or similar groups in the polymer which are hydrophilic. In general it is preferred that the cationic groups be present in polymers which have substantial polysurfactant character as in polymers with moieties of substantial hydrophobic nature such as copolymers of olefins of 6 or 8 or so carbon atoms up to 20 or more. Some such polymers have been described hereinabove and will now be further exemplified.

A particular class of derivatives of maleic acid/-C₄-C₂₂ mono-olefin copolymers includes the aminoamides, the aminoimides and salts that can be derived from them. These classes of polyelectrolytes can further be converted to useful polymers containing a quaternary nitrogen atom. The aminoamides can be represented by the formula

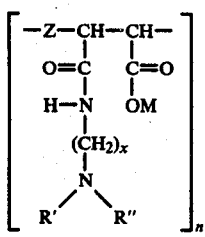

wherein Z and n are as defined above, x is an integer from 1 to 5, R' and R" are each alkyl radicals of from 1 to 5 carbon atoms, and M is hydrogen, ammonium radical, or a metallic ion of an alkali or alkaline earth metal.

The polymeric materials containing the aminoamide linkage as illustrated above can be converted to the corresponding aminoimide by heating at 100 degrees to about 170 degrees centigrade, preferably at 130 degrees to 150 degrees centigrade to give the polymer corresponding to the formula

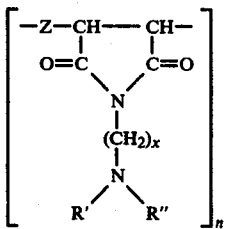

wherein Z, n, x, R' and R" are as described above.

The aminoamides and aminoimides derived from the maleic acid/$C_4$–$C_{22}$ mono-olefin copolymers are useful herein; however, they may be further modified by conversion of at least a portion of the tertiary nitrogen atoms to quaternary nitrogen atoms. In certain instances the copolymer containing the tertiary amide linkages can also be employed as the amine hydrohalide salt by treatment with a hydrogen halide, e.g., HCl. The quaternary ammonium derivatives are readily prepared by reaction with an alkyl halide of the formula R''' X, where R''' is an alkyl radical of 1 to 18 carbon atoms and X is a halogen atom. Aralkyl halides, such as benzyl halide, can also be used to prepare the quaternary ammonium salts. These useful derivatives can be represented by the formulas

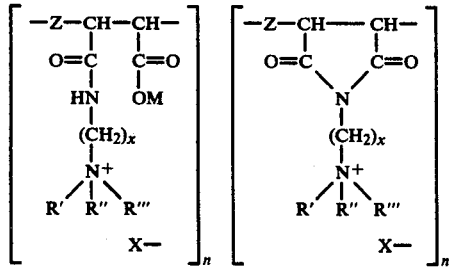

wherein Z, M, n, x, R' and R" are as described above, R''' is an alkyl radical of 1 to 18 carbon atoms or an aralkyl radical of 7 to 12 carbon atoms and X is a halogen atom. As illustrative of copolymers having the above formulas may be mentioned the diethylaminoethyl amide of maleic acid-ethylene, 1-butene, or styrene copolymer, the dimethylaminopropyl amide of maleic acid-ethylene, 1-hexene, 1-octene, or styrene copolymer, ammonium salt, the dipropylaminoethyl imide of maleic acid ethylene, propylene, or styrene copolymer, the dimethylaminopropyl amide of maleic acid-ethylene, octene, or styrene copolymer, as the methyl iodide quaternary salt, or the octadecyl bromide quaternary salt of diethylaminobutyl imide of maleic acid-ethylene, propylene or styrene copolymer.

In providing the desired polymers, ethylenic monomers of the requisite number of carbon atoms can be selected for polymerization with the maleic anhydride prior to formation of derivatives, for example hydrocarbons of 8 or more carbon atoms, vinyl ethers of 8 or more carbon atoms, etc. While the above is illustrated with maleic copolymers, it will be recognized that carboxylic acid groups from other monomers provide a basis for aminoamide and quaternary salt derivatives, and such is contemplated with regard to the other carboxylic acid polymers taught herein. However, a particular class of cationic polymers for use herein can be described as alkene/maleic copolymers containing di-lower alkylaminoloweralkylamide or diloweralkylaminoloweralkylimide groups, or the acid addition or quaternary ammonium salts thereof, and it is preferred that the alkene group has 8 or more carbon atoms. Such class can also include such alkene/maleic copolymers in which the cationic group is a diloweralkylaminoloweralkyl ester group or the acid addition or quaternary ammonium salt thereof. It will be recognized that the polymers can have a combination or mixture of different cationic or other groups, and that such derivatives may be formed from only part of the carboxyl groups present in the polymer, and further, that a mixture of olefinic groups can be present in the polymer. The polymers herein may have varying portions of available carboxyl groups converted to any of the cationic groups described above, e.g., 2 to 100%, and be particularly effective for the purposes of the present invention. However, in view of the importance of cationic groups for such purposes, there may be advantage in utilizing polymers with at least 50% conversion to such derivatives, or even 70% or more. In a polymer typically containing 25 to 75% carboxylic acid moiety on a molar basis, this provides a fairly good concentration of cationic groups. In the event amine and carboxyl groups, for example, form amine salts, such as probably not cationic; in such event it is advisable to have an excess of the amine or other cationic groups, and the cationic character is then determined by the excess of cationic groups and resulting net charge.

Some of the polymers utilized herein are characterized by a comparatively high degree of water solubility and/or dispersibility and are well adapted to perform in physiological media.

What is claimed is:

1. A method of countering a tendency toward obesity in a subject in need thereof which comprises orally administering to such subject an effective amount of non-absorbable polymerized unsaturated carboxylic acid or pharmaceutically acceptable derivative thereof sufficient to cause increased fat excretion, the polymer being a cationic derivative of an olefin-maleic acid copolymer of molecular weight of about 3000 to about 1,000,000 which is an effective pancreatic lipase inhibitor.

2. The method of claim 1 in which the polymer has a $pK_a$ no less than 6.

3. The method of claim 1 in which the polymer is a diloweralkylaminoalkylamide or diloweralkylaminoimide or acid addition or quaternary ammonium salt forms thereof, of alkene/maleic acid copolymers in which the alkene has at least 6 carbon atoms.

4. The method of claim 1 in which the polymer is in quaternary ammonium salt form.

* * * * *